United States Patent

Härle

[11] Patent Number: 5,769,897
[45] Date of Patent: Jun. 23, 1998

[54] SYNTHETIC BONE

[76] Inventor: Anton Härle, Drechslerweg 40, D 48161 Muenster, Germany

[21] Appl. No.: 203,268

[22] Filed: Feb. 28, 1994

Related U.S. Application Data

[63] Continuation-in-part of Ser. No. 808,191, Dec. 13, 1991, abandoned.

[51] Int. Cl.⁶ .......................................... A61F 2/28
[52] U.S. Cl. ................. 623/16; 623/17; 606/60; 606/76
[58] Field of Search .................. 623/16, 17; 606/76, 606/77, 60; 424/423, 426; 523/114, 115

[56] References Cited

U.S. PATENT DOCUMENTS

| | | |
|---|---|---|
| 2,621,145 | 12/1952 | Sano . |
| 2,968,593 | 1/1961 | Rapkin . |
| 3,090,094 | 5/1963 | Schwartzwalder et al. . |
| 3,458,397 | 7/1969 | Myers et al. . |
| 4,172,128 | 10/1979 | Thiele et al. . |
| 4,294,753 | 10/1981 | Urist . |
| 4,643,735 | 2/1987 | Hayes et al. . |
| 4,834,757 | 5/1989 | Brantigan . |
| 4,950,296 | 8/1990 | McIntyre ................................. 623/16 |
| 5,263,985 | 11/1993 | Bao et al. ................................ 623/16 |
| 5,281,419 | 1/1994 | Tuan et al. ............................... 623/16 |
| 5,425,772 | 6/1995 | Brantigan ................................ 623/17 |
| 5,458,638 | 10/1995 | Kuslich et al. ........................... 623/17 |
| 5,593,409 | 1/1997 | Michelson ................................ 623/17 |
| 5,609,635 | 3/1997 | Michelson ................................ 623/17 |

FOREIGN PATENT DOCUMENTS

| | | |
|---|---|---|
| 0353476 | 2/1990 | European Pat. Off. . |
| 2242867 | 5/1974 | Germany . |
| 3106917 | 11/1982 | Germany . |
| 3435771 | 4/1985 | Germany . |
| 3445738 | 6/1986 | Germany . |
| 3615732 | 11/1987 | Germany . |
| 3903832 | 8/1990 | Germany . |
| WO/87/07827 | 12/1987 | WIPO . |
| WO/88/01517 | 3/1988 | WIPO . |
| WO/90/00037 | 1/1990 | WIPO . |

OTHER PUBLICATIONS

Algae–Derived (Phycogene) Hydroxylapatite by Kasperk et al. May 9, 1988, Research; Development.
Porosity and Specific Surface of Bone by R. Bruce Martin CRC Critical Reviews in Biomedical Engineering, vol. 10 pp. 179–222.
Endobon, Sep. 1991 by Merck.

*Primary Examiner*—Paul B. Prebilic
*Attorney, Agent, or Firm*—Peter K. Kontler

[57] ABSTRACT

An artificial (namely synthetic) bone material is made up of a strength sustaining first component and of a biointegration promoting second component. The first component is made, for example of a bioceramic material providing a material strength, especially a compression strength, of at least 1000 N/cm². The second component is made also of bioceramic material or even of bone tissue or it may contain bone tissue in combination with other biointegration enhancing components. Biointegration is greatly improved if the material of the second component comprises a specific surface of at least 1.5 m²/gram. The second component is incorporated in accessible voids such as open cells, pores, bores, holes and/or other cavities of the first component, whereby the first component forms a frame or matrix for the second component and imparts to the artificial bone the required strength prior to, during, and after implantation. The artificial bone material, due to its accessible voids in the first component and capillary ducts in the second component can receive one or more pharmaceutical substances. The material is formed to have a wedge shape for replacing or complementing a damaged or destroyed natural bone or a portion of a bone. The second component can fully or partly disintegrate upon completion of the implanting to promote penetration of freshly grown bone tissue into the first component.

24 Claims, 3 Drawing Sheets

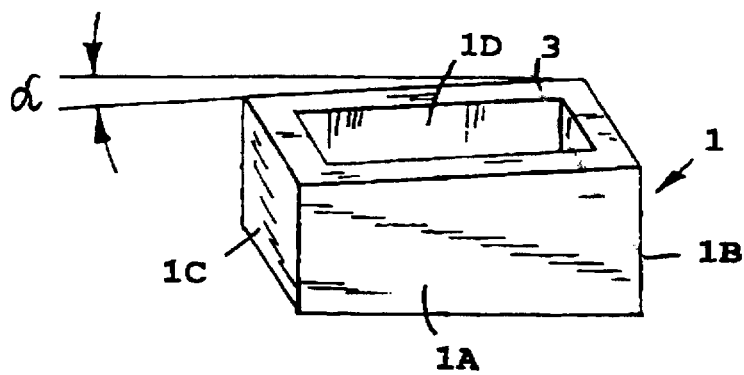
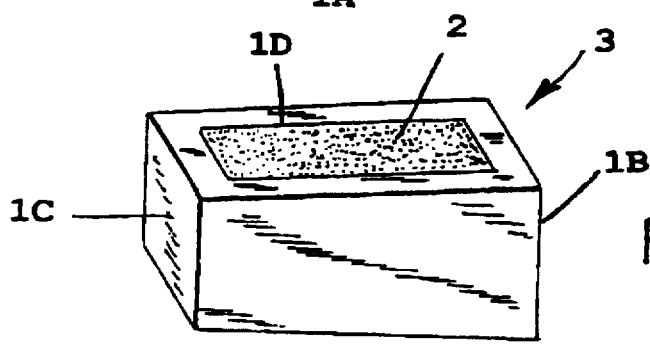
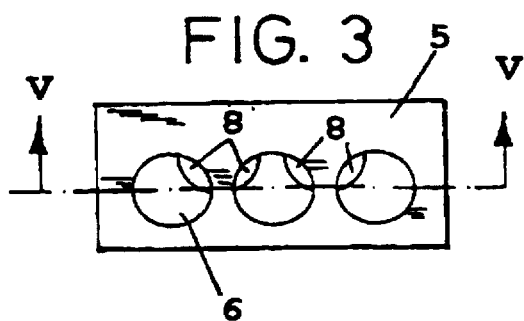
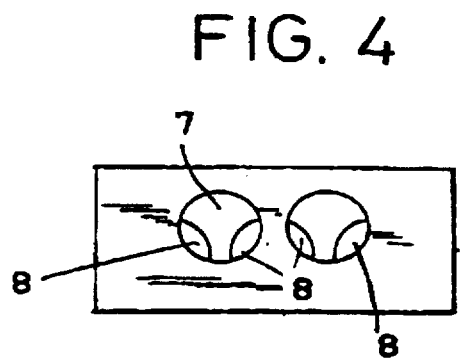
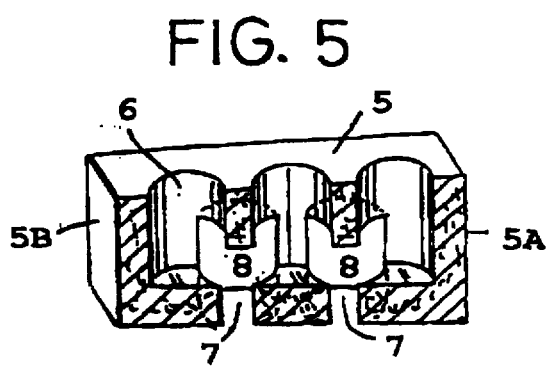
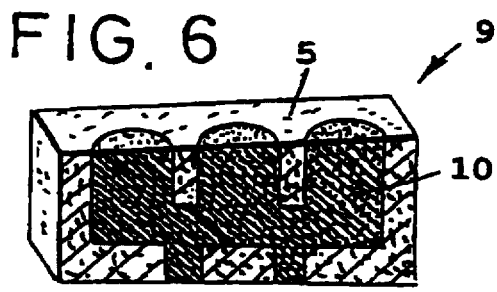

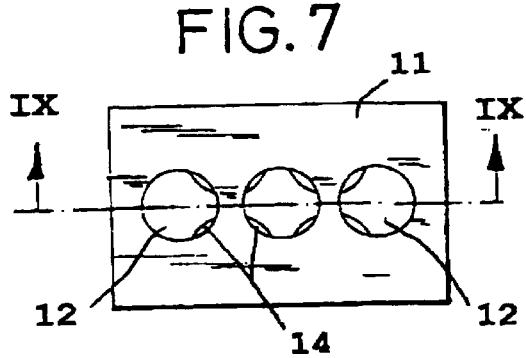
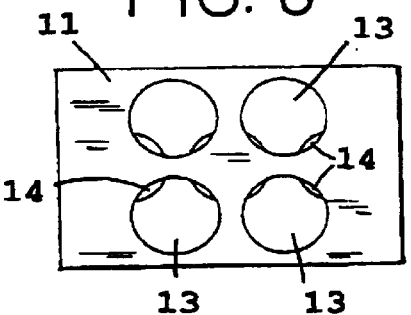
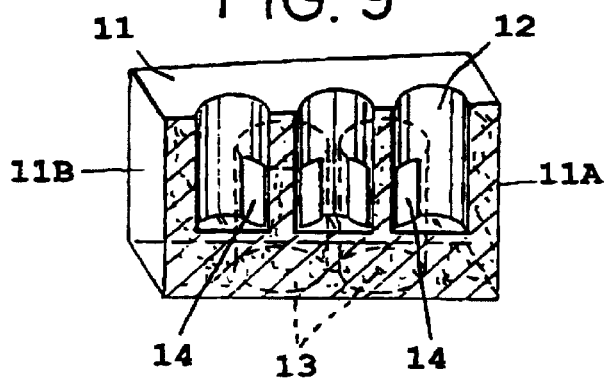
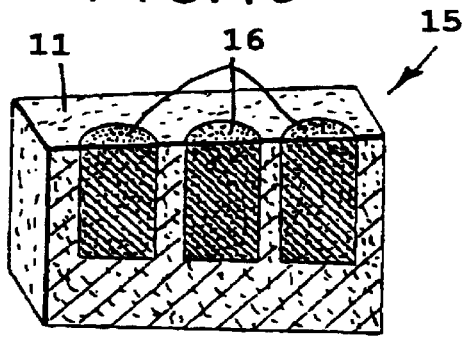
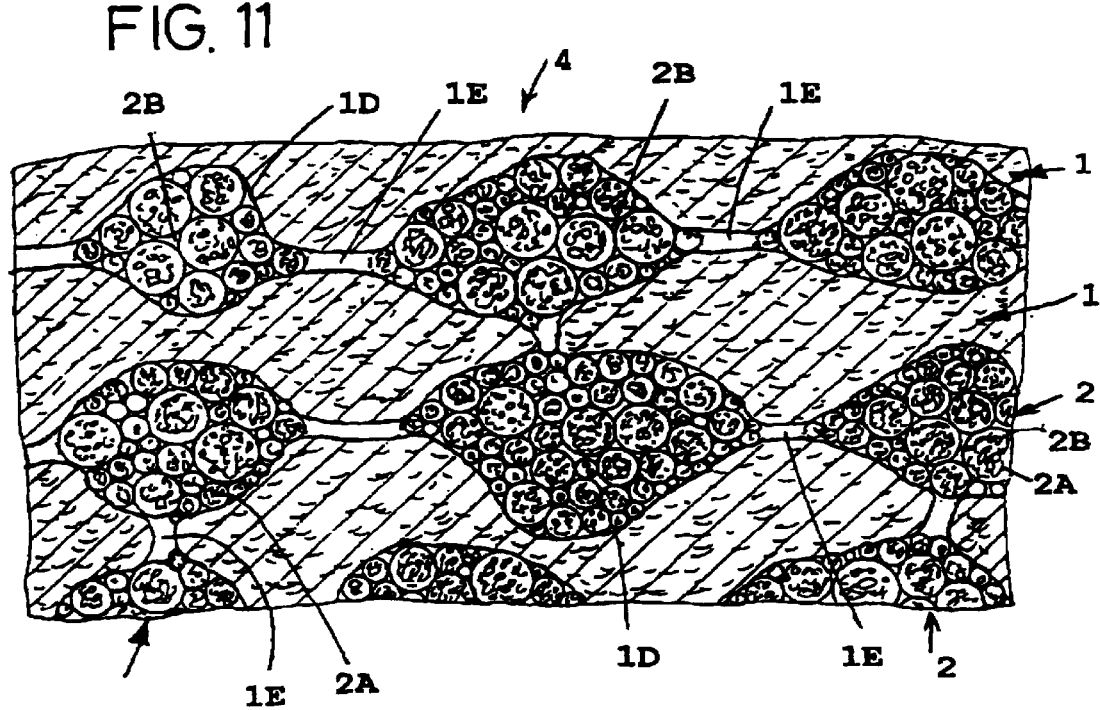

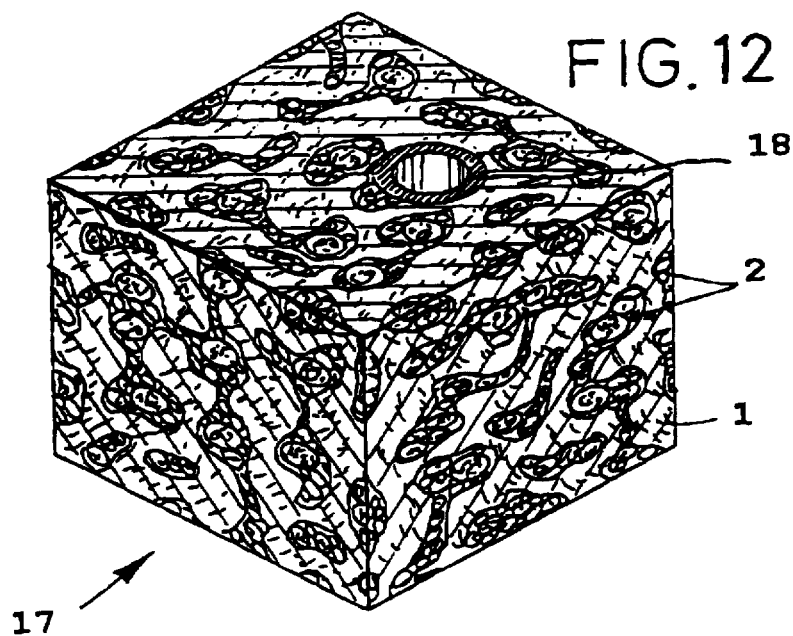
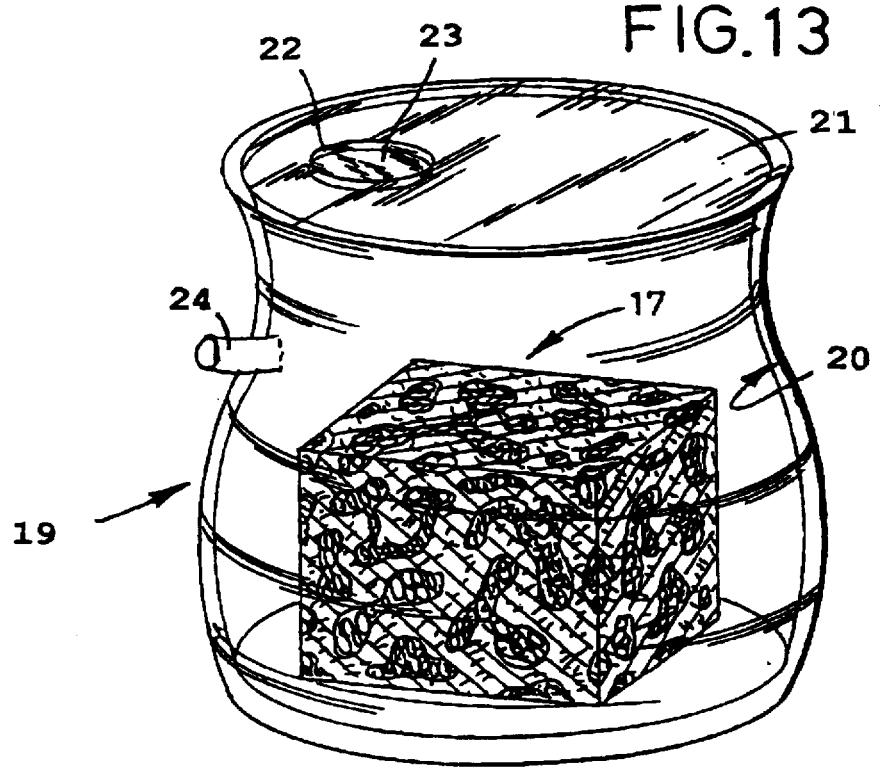

SYNTHETIC BONE

CROSS-REFERENCE TO RELATED APPLICATION

This application is a Continuation-In-Part application of my U.S. Ser. No.: 07/808,191, filed on Dec. 13, 1991 now abandoned.

FIELD OF THE INVENTION

The invention relates to improvements in artificial bone materials, and bodies made of these materials which can be used to form pieces of or entire artificial bones for implantation. The invention also relates to methods of making, storing and treating the artificial bone material prior to implantation.

BACKGROUND INFORMATION

Reconstructive medical treatments make extensive use of artificial bones and of materials which can be used for the restoration and/or building of bone portions or of entire bones. One of the reasons for such use is that the autologous bone tissue is often insufficient and the surgeon must take into consideration the risk of development of a disease at the locus of removal of autologous bone tissue.

Further, the development of hydroxy apatite ceramics for use in lieu of a basic bone substance has failed to meet the expectations in spite of extensive research and development work, particularly in the last two decades. Numerous known artificially produced bioceramic materials exhibit different degrees of solubility and resorptivity. However, save for a few notable exceptions, known artificial bone materials failed to replace autologous bone transplants. In fact, hydroxy apatite ceramics failed to make even a small dent in the quantities of autologous bone materials which are being used for implants. It is believed that the main reason for the failure of presently known artificial bones and artificial bone materials to gain wider acceptance in the field of bone implantation, is the unsatisfactory material strength of heretofore known artificial materials to withstand mechanical loads. In cases where the material strength is acceptable the inability of artificial bone material to become integrated in the body tissue of a patient is a problem. Conventional artificial bone materials fail to be sufficiently biodegradable for the integration.

If an implanted substitute bone is to withstand mechanical loads, such an implanted bone must establish an intimate and load resistant connection with or biointegration into the existing, natural bones. Biointegration can be achieved only as a result of a partial dissolution or biodegradability of the implanted artificial bone to permit new bone formation at the surface of the implant. Hence, biodegradability is a primary requisite for such an integration of implanted artificial bones into existing natural bones. However, the implanted artificial bone is also expected to withstand mechanical loads, at least during the period of insufficient stability of the natural bones as a result of biointegration and new bone formation.

In view of the above, an artificial bone is expected to meet two requirements which were believed to be mutually exclusive or incompatible requirements, because an implantable material with a sufficient mechanical strength conventionally does not have the required biodegradability while a conventional material with the required biodegradability does not have the needed mechanical strength. This incompatibility has posed a substantial problem that has not been solved by the prior art.

U.S. Pat. No. 3,090,094 (Schwartzwalder et al.) issued on May 21, 1963, discloses a method of manufacturing open-celled, porous ceramic structures which can be used in heat-resistant filters for molten metal and/or as heat-resistant catalyst supports. The method involves immersing an open-celled element of spongy material in a slurry containing a ceramic coating material for coating the cell-defining walls of the open-celled element, removing excess slurry, and firing the element to remove the slurry and form a hardened porous ceramic structure. Schwartzwalder et al. do not suggest using the hardened porous ceramic as an implant to replace a bone or a portion of a bone in a human or animal body.

U.S. Pat. No. 4,172,128 (Thiele et al.), issued on Oct. 23, 1979, discloses a complex process for degrading and reconstituting bones or teeth by demineralizing natural bone or tooth material which is obtained from animals, converting the demineralized material into a mucopolysaccharide-free colloidal solution, adding a physiologically inert foreign mucopolysaccharide, gelling the solution and remineralizing the resulting gel.

U.S. Pat. No. 2,968,593 (Rapkin), issued on Jan. 17, 1961, discloses a preparation of anorganic bone material which is obtained by heating bone in a liquid to 80–100° C., drying and substantially defatting the bone with a fat extracting solvent, and removing the organic matrix from the defatted bone to obtain an inorganic matrix.

U.S. Pat. No. 2,621,145 (Sano), issued on Dec. 9, 1952, discloses a bone mat composition formed as a roll to be used in bone surgery to promote regrowth of bone. The bone mat is made of a rolled flexible strip consisting of a multiplicity of unboiled particles of ground whole bone enmeshed in and held together by a fibrin network.

U.S. Pat. No. 4,294,753 (Urist), issued on Oct. 13, 1981, discloses a bone morphogenetic protein (BMP) process which involves separation of BMP from bone tissue by demineralizing bone tissue, treating the demineralized bone tissue under aqueous conditions with a water-soluble neutral salt and a solubilizing agent for BMP, and separating the solubilizing agent and neutral salt from the solution to thereby precipitate BMP in the aqueous medium.

U.S. Pat. No. 3,458,397 (Myers et al.), issued on Jul. 29, 1969, discloses a process for producing osteogenic material from animal bone tissue. Ground cancellous bone is treated with pepsin in acid solution, and the digested material is subjected to extraction and precipitation prior to freeze drying of the resulting extract. The dried extract can promote bone formation in vivo when injected at sites of bone defects or disorders along the periosteal membrane of the bone.

German Patent Publication No. 3,106,917, (Grundei), published on Nov. 25, 1982, discloses an implantable artificial bone consisting of a shape-retaining spongy material with open pores or cells. Grundei further discloses various methods of making the spongy material.

German Patent Publication No. 3,903,832, (Taeger) published on Aug. 16, 1990, discloses a hip joint prosthesis wherein the cupped part of the prosthesis is provided with openings for reception of bone tissue in order to promote the growth of new bone substance.

German Patent Publication No. 3,435,771 (Gendler), published on Apr. 25, 1985, discloses a bone matrix and a method of making the matrix in such a way that it induces the growth of bone. The matrix is formed with a number of holes prior to the implanting step to promote the ingrowth of cells and veins subsequent to implantation.

German Patent Publication No. 3,615,732 (Franek et al.), published Nov. 12, 1987, and corresponding to PCT WO 87/06842, discloses a composite substance for the making of prostheses and a method of making such substance. The composite substance comprises a metallic component and at least one bioactive substance which is embedded in the metallic component. The bioactive substance contains at least one anorganic-chemical component, and the ratio of metallic component to bioactive substance is preferably 7:3.

German Patent Publication No. 2,242,867 (Heide et al.), published May 2, 1974, discloses a method of making implantable artificial bones of a ceramic material. The method involves assembling spherical particles into a porous body, the pores of which are filled with a flowable mass of ceramic material which is caused to set before the spherical particles are removed and/or dissolved to leave a ceramic mass having a shape corresponding to that of the pores in the destroyed body of assembled spherical particles.

German Patent Publication No. 3,445,738 (Draenert), published Jun. 19, 1986, discloses an implantable socket for holding of bone screws. The socket can be expanded in the body of a patient, e.g., by swelling, or can be provided with a thread to mesh with an original bone and to provide a bore for the reception of a bone screw or another implantable part.

European Patent Publication 0,353,476 A3 (Nonami et al.), published on Feb. 7, 1990, discloses a biomedical material and method for making such a material which is formed as a sintered composite having a crystalline calcium phosphate matrix and inorganic whiskers dispersed or embedded in the matrix. The whiskers are selected from the group of silicon oxide, aluminum oxide, calcium oxide, and magnesium oxide. The matrix is tricalciumphosphate or apatite with a preferred grain size within the range of 0.05 to 30 $\mu$m. The whiskers which are, for example naorthite and diopside whiskers take up about 0.5 to 95% of the area of a cross-section of the sintered body. The whiskers have a preferred length of 0.05 to 30 $\mu$m and an aspect ratio within the range of 1.2 to 100. The ratio of matrix grain size to the whisker length is within the range of 10 to 1 to 1 to 10. Such a sintered composite material has the required toughness and strength while also apparently providing a certain biomedical affinity.

PCT Patent Publication WO 90/00037 (Michaelson), published on Jan. 11, 1990, discloses artificial spinal fusion implants capable of fusion to two neighboring vertebrae in the spine. The implant is a rectangular member having a plurality of openings therein for promoting bone ingrowth with the implant and fusion of the vertebrae. These implants have macro sized cells and openings within the range of 1 to 3 mm which can be loaded with fusion promoting materials, such as autogenous bone for influencing the adjacent vertebrae to enter into a bony bond to the implants and to each other. Michaelson teaches making the implants of materials that are stronger than bone.

PCT Patent Publication WO 88/01517 (Toermaelae et al.), published on Mar. 10, 1988, discloses a bone graft implant having a supporting structure for preventing movements of powder materials used as a bone graft powder. The powder supporting structure is located in contact with bone tissue and is manufactured at least partially of resorbable polymer, copolymer, or polymer mixtures. The supporting structure has a shape of a chute or trough or of a box or a flat tube or bag and contains an open porosity which allows the surrounding tissue to grow through the supporting structure. The porosity prevents the migration of bone graft powder through the pores out of the supporting structure. A larger opening in contact with the bone permits the growth of bone tissue into the supporting structure.

PCT Patent Publication WO 87/07827 (Grundei et al.), published Dec. 30, 1987, discloses an implant for securing two adjacent vertebrae. The implant is made as a cylindrical or tubular open-cell metal body which has a solid construction at least at the proximal end forming the operative surface for impacting with a striking tool. The implant is open-celled and can have the shape of a frustum with inclination angles within the range of 4° to 80°.

U.S. Pat. No. 4,643,735 (Hayes et al.), issued on Feb. 17, 1987, discloses repair material for the reconstruction of bones. The repair material is polydivinylbenzene in particulate form, whereby the particles have random sizes and are relatively porous with a relatively high specific surface area of at least 150 $m^2$/g of the particulate material and a specific weight of about 0.3 to 0.45 $g/cm^2$.

U.S. Pat. No. 4,834,757 (Brantigan), issued on May 30, 1989, discloses prosthetic implant plug constructed as supports and for fusing together neighboring vertebrae. The plugs are rectangular with tapered front ends and tool receiving ends. The longitudinal edges are provided with sawtooth like protrusions for anchoring purposes. Materials suitable for making such plugs are inert metals, such as stainless steel, titanium, cobalt, chromium molybdenum alloys and the like. Radiolucent materials transparent to X-rays also, such as plastics of the nylon, polycarbonate, polypropylene, polyacetyl, polyethylene, and polysulfone types may also be used for making the plug, preferably with the synthetic material forming a matrix filled with glass or carbon fibers. The plugs can, for example, be injection molded.

An article entitled "Porosity and Specific Surface of Bone" by R. Bruce Martin, published in "CRC Critical Reviews in Biomedical Engineering", Vol. 10, pages 179 to 222; 1984; describes porosity and specific surface as two most important features of the internal structure of bone. Martin indicates that porosity is a dimonsionless ratio while "specific surface", has dimensions of $cm^2$ /$cm^3$ or per cm length. Martin has found that small increases in porosity produced significant decreaseg in relative bone strength. Martin has also found that a bone region having a specific surface, for example of 5 $mm^2$/$mm^3$ has a much greater potential for remodeling than a bone region with a specific surface of only 1 $mm^2$/$mm^3$. Martin's definition of the specific surface area does not provide a critical distinction between porosity which takes into account the volume of all voids, open and closed, relative to total volume and specific surface area which he sees as the internal surface area per unit volume regardless of whether or not that internal surface area is available for reaction, that is, for biointegration. Martin merely recognizes that the rate of change of the porosity will be influenced by the amount of internal surface that is available for physiologic activity.

An article entitled "Algae-derived (phycogene) Hydroxylate—A Comparative Histolocgical Study" by C. Kaeperk et al. published in the "International Journal of Oral Maxillofac Surgery"; May, 1988, describes granular hydroxylapatite (HA) biomaterials which produce a characteristic pattern of bone healing. The bioceramics provide a dense bone-implant interface provided that a large specific surface area is available in the implant which favors osteoneogensis and cell spreading onto and into an implant.

The disclosure of the above discussed publication is incorporated herein by reference as part of the enabling disclosure. The above described prior art has not solved the problem of the incompatibilty between material strength on the one hand and a good biodegradability on the other hand. Therefore, there is room for improvement.

OBJECTS OF THE INVENTION

In view of the above, it is the aim of the invention to achieve the following objects singly or in combination:

to provide an artificial namely synthetic bone material which satisfies the above mutually exclusive requirement or characteristics of mechanical strength and biodegradability simultaneously and without impairment of one characteristic by the other and vice versa;

to provide a biodegradable artificial bone which has a pronounced mechanical strength while simultaneously enhancing the growth of natural bone material into and onto the artificial material;

to provide an artificial bone material that can be easily shaped, for example by a surgical instrument, to any desired implant configuration, including an entire natural bone or a relatively small or a larger section of a natural bone including vertebrae and parts thereof;

to provide an artificial bone material which can be stored for extended periods of time and which can be used as a carrier of medications which are to be distributed in the body of a patient upon implantation of the artificial bone;

to provide an artificial bone which can be fully integrated into an existing natural bone;

to provide an artificial bone material which has, in addition to its mechanical strength, a biodegradability that substantially enhances the biointegration of an implant made of such materials into a natural bone;

to provide an artificial bone material that is especially suitable for repairing or replacing a disc in a spinal column;

to provide a novel and improved method of storing artificial bone material which exhibits the above outlined characteristics;

to provide a novel and improved method of treating artificial bone material prior to implantation into a body; and to provide a method of making artificial bone material that simultaneously has the required mechanical strength and biodegradability.

SUMMARY OF THE INVENTION

The above objects have been achieved by the provision of an artificial namely syntheitic, bone material that, according to the invention, has two components. A first component is constructed for sustaining the mechanical strength of the material while a second component is constructed as a component for enhancing biointegration with the natural bone tissue when the material is, for example, implanted as a bone replacement or partial bone replacement. The first component is made of at least one first biomaterial having at least a compression strength of at least 1000 N/cm$^2$. The second component is S made of at least one second biomaterial having open pores providing a specific surface of at least 1.5 mm$^2$/g for sustaining biointegration. The first component has at least one accessible void. The second component is incorporated in the void of the first component so that an integral structure is provided.

The term "specific surface" as used herein defines a surface area that is available for reaction to cause biointegration per unit of weight of the second component material, The term takes into account inner and outer surface areas of the second component that are directly accessible for the blointegration. For example, such a reactive surface area would be directly accessible to a gas absorption. Thus, the specific surface relates to open pores, cells, voids, etc. that are interconnected so that these surfaces can participate in the biointegration. The present inventor has recognized that fully closed cells, pores, voids or the like on or in the biomaterial cannot participate in the biointegration and hence must be excluded from the specific surface to provide a useful measure for achieving the intended biointegration. Porosity is not useful in this respect, because it takes all voidws into account regardless of whether they are closed or open.

According to the invention, the first and second biomaterials can be selected from a group including bioceramic materials, carbon ceramics, aluminum oxide ceramics, glass ceramics, tricalciumphosphate ceramics (TCA), tetracalciumphos-phate ceramics, hydroxylapatite (HA), polyvinylmethacrylate, titanium, implantation alloys, and biocompatible fiber composite materials. In a preferred embodiment the first and second components are made of hydroxylapatite ceramic (HA) and/or of tricalciumphosphate ceramic (TCA). In all instances the construction will be such that the first component has at least one, preferably a plurality of relatively large accessible voids with dimensions in the range of 1 to 5 mm, while the biomaterial of the second component will have open micropores having dimensions within the range of 10 to 300 $\mu$m. Any conventional methods for producing the large voids or macropores in the first component and the micropores in the second component are suitable for the present purposes. For example, different conventional sintering processes and milling processes for making the bioceramics will provide the large and small accessible pores with the desirable dimensions.

The first strength sustaining component is preferably constructed as a tubular or honeycomb structure having accessible tubular voids or honeycomb cells in which the second component is incorporated. The accessibility to voids in the first component is needed for the incorporation or integration of the second component into the first component. The openness of the micropores in and on the second component is necessary for the biointegration. Further, the open individual voids and pores are interconnected in the first and second component by ducts, passages, or channels to enhance the facility of introduction of the second component into the first component when the latter is incorporated into the first component, and to enhance the growth of natural bone into and onto the second component for the biointegration.

According to the invention, the first component has a first biodegradability which is sufficiently small to sustain the required compression, and preferably also a required tensile strength and shear strength for prolonged periods of time while the second component has a second biodegradability substantially larger than the first biodegradability and sufficient to sustain the biointegration. For example, the second biodegradability should be at least 20 times larger than the first biodegradability. The biodegradability can be adjusted conventionally, depending on the solubility of the second component material in water or in enzymes. A further important adjustment factor for the biodegradability as taught herein is the selection of the specific surface. Porosity is merely relevant to the material strength given herein in Newton (N) per square centimeter.

BRIEF DESCRIPTION OF THE DRAWINGS

In order that the invention may be clearly understood, it will now be described, by way of example, with reference to the accompanying drawings, wherein:

FIG. 1 is a perspective view of one embodiment of the first component of an artificial bone material according to the invention having one accessible void;

FIG. 2 is a view similar to that of FIG. 1, but further illustrating the second component of the present artificial bone material incorporated into the void of the first component;

FIG. 3 shows a top plan view of a second embodiment of the first component;

FIG. 4 is a bottom plan view of FIG. 3;

FIG. 5 is a sectional view taken along the line V—V in FIG. 3, illustrating the wedge-shape or cuneiform of the present form bodies;

FIG. 6 is a view similar to that of FIG. 5, but illustrating the second component upon incorporation into the first component;

FIG. 7 is a top plan view of a third embodiment of the first component;

FIG. 8 is a bottom plan view of the first component of FIG. 7;

FIG. 9 is a sectional view taken along the line IX—IX in FIG. 7, again illustrating the cuneiform or wedge shape of the first component;

FIG. 10 is a sectional view as in FIG. 9, and further illustrates the second component upom incorporation into the first component;

FIG. 11 is a sectional view through a portion of an artificial bone material according to the invention illustrating the incorporation of the second component into the accessible voids of the first component which latter forms a supporting frame structure for the second component and sustains biointegration;

FIG. 12 is a perspective view of an artificial bone material body according to the invention, provided with an anchoring device; and FIG. 13 shows a vacuum vessel for treating, storing and transporting the artificial bone material according to the invention prior to implantation.

DETAILED DESCRIPTION OF PREFERRED EMBODIMENTS AND OF THE BEST MODE OF PRACTICING THE INVENTION

FIGS. 1 and 2 show a first embodiment of the invention. A mechanical strength sustaining first component 1 made of the artificial bone material of the invention comprises a form body 1A having a wedge-shaped configuration with a large end 1B and a small end 1C, thereby forming a wedge angle a which is within the range of 2° to 19°, preferably within the range of 2° to 5°. This wedge-shaped configuration greatly facilitates the use of the present artificial bone material for surgical replacement or repair of vertebrae. The first component 1 has at least one void 1D which is externally accessible for incorporating the second component 2 of biomaterial in the void iD to form an artificial bone material in the form of a preformed form body 3.

Each of the biomaterials for forming the first component 1 and the second component 2 can be selected from the above listed materials, whereby tricalcium phosphate ceramics (TCA) and hydroxylapatite ceramics (HA) are preferred for making the first and/or second component. Thus, one component can be made of TCA while the other is made of HA or vice versa. Both components could be made of TCA or of HA provided that the conditions of the invention are satisfied, namely that the first component 1 has a sufficient material strength of at least 1000 N/cm$^2$ and the second component has a specific surface of at least 1.5 m$^2$/g available for reaction to sustain biointegration. The required material strength is obtained by a respective treatment of the starting material, for example, by conventional sintering processes to obtain the required density to particularly sustain the claimed compression strength. Similarly, the required specific surface area available for reaction is obtained by treating the starting material accordingly, for example, by forming a granular material in which the granules have a certain size, for example, within the range of 0.3 to 3 mm. The granules then contact each other to form open micropores interconnected between neighboring granules so that the specific surface area as defined above, is at least 1.5 m$^2$/g.

Each of the first and second biomaterials has a certain biodegradability. However, the biodegradability of the first component material must be sufficiently small to sustain the compression strength of at least 1000 N/cm$^2$. The biodegradability of the second component must be substantially larger to sustain the biointegration. It has been found that an average biodegradability of the listed materials is suitable for the intended biointegration but is much too high for sustaining the claimed mechanical strength. It is preferable that the biodegradability of the second component is at least about 20 times that of the first component. In other words, the biodegradability of the first component must be substantially below average.

FIG. 11 is an enlarged sectional view through an artificial bone material according to the invention, wherein the first component 1 forms a skeletal supporting structure 4 that may either be a honeycomb structure or a tubular structure. In both instances, an open cellular structure is provided. The voids 1D which are at least partially initially accessible are filled with the second component 2. Additionally, the accessible voids 1D in the first component 1 are interconnected through passages or tubular channels 1E, whereby substantially all voids become accessible, for example, for gas evacuation prior to incorporation of the second component into the first component. The second component 2 comprises a plurality of granules 2A which form interconnected micropores 2B between neighboring granules. The accessible voids or open cells 1D in the first component 1 in the form of a bioceramic material form macropores with dimensions within the range of 1 to 5 mm. On the other hand, the bioceramic material of the second component has open micropores 2B with substantially smaller dimensions, namely in the range of 10 to 300 µm, whereby the micropores are also interconnected by capillary ducts having a capillary duct diameter of about 20 µm or less. The communication established by these micropores and capillary ducts in the second component 2 greatly facilitates the biointegration. Instead of being made of a bioceramic, the second biomaterial may also be made of a natural bone tissue, whereby autologous bone tissue is preferred.

In connection with FIG. 11, it should be mentioned that the total volume of accessible voids in the macroporous bioceramic material of the first component 1, must be smaller than a porosity that would impair the strength of at least 1000 N/cm$^2$ of the first component. In other words, the bioceramic material of the first component has a minimal solids volume sufficient to sustain the required strength of at least 1000 N/cm$^2$. The illustration of FIG. 11 shows a tubular or honeycomb structure in which the accessible voids 1D with the interconnecting channels 1E form tubular, accessible, open cells in which the second component material 2 is incorporated or integrated, as described.

FIGS. 3, 4, 5 and 6 show a second embodiment comprising a first component 5 with three accessible voids 6 in its top surface, and two accessible voids 7 in its bottom surface as shown in FIG. 4. These voids 6 and 7 in the body of the first component 5 are so positioned that there is an overlap forming a passage or channel 8 enabling all voids 6 and 7 to communicate with each other. The voids 6 and 7 are preferably blind bores which enter into the body of the component 5 from opposite surfaces to the extent of the desired overlap shown at 8. As shown in FIGS. 5 and 6, the first component 5 is also a shaped body having a wedge configuration with a large end 5A and a small end 5B. FIG. 6 shows the co mpleted artificial bone material 9 with the second component material 10 incorporated into the body 5.

FIGS. 7, 8, 9 and 10 illustrate a third embodiment in which the first component 11 has three voids 12 in its top surface and four voids 13 in its bottom surface. These voids 12 and 13 are also preferably dead-end or blind bores which are so positioned in the body of the first component 11 that a p artial overlap 14 is assured to establish the required accessibility and communication between neighboring voids or bores.

FIG. 9 shows that the body of the first component 11 of the third embodiment has a wedge shape with a large end 1A and a small end 11B. The overlap 14 provides the required communication between the bores or voids 12 and 13. In FIG. 10, the material of the second component 16 is incorporated into all bores 12 and 13. However, the bores or voids 13 are not seen in FIG. 10 because voids 13 are positioned behind the section plane.

The communication or accessibility provided by the overlaps 8 in the second embod iment of FIGS. 3 to 6 and by the overlaps 14 in the third embodiment of FIGS. 7 to 10 is important for the incorpor ation of the second component into the first component and also for the integration of the implant into the natural bone through the capillary ducts 2B which for m a communication s network or rather an integration network through the overlaps 8, 14.

FIG. 12 shows an artificial bone material body 17 that can, for example, be cut with a surgical saw from the bone material shown in FIG. 11. A fastening device 18 is embedded in the bone material of the body 17. The fastening device 18 may, for example, be a tubular socket or it may be a dowel firmly embedded in the body 17 for cooperation during the implantation surgery with a further fastening device, such as a pin, stud, screw, or other threaded fastener in the form of a bolt or nut.

FIG. 13 illustrates a vacuum vessel 19 defining a vacuum chamber 20 in which the body 17 is stored according to the invention under a reduced pressure. The vacuum vessel 19 has a cover 21 which in turn has an opening 22 sealed, for example by a membrane 23 made of an elastomeric plastic or rubber material that is selfsealing, e.g. around an injection needle, not shown, that punctures the membrane 23 to introduce a pharmaceutical substance into the chamber 20. The pharmaceutical will enter into the capillary ducts 2B shown in FIG. 11 due to the reduced pressure therein. The vacuum vessel 19 is preferably provided with a valve 24 that may also function as a coupling, preferably a quick coupling device, for connection to a vacuum pump, not shown, to evacuate the chamber 20 in the vessel 19 to a properly reduced pressure, such as 0.3 bar. In addition to, or instead of the pharmaceutical, another treatment substance, such as radio isotopes and cytostates may be introduced through the membrane 23 by penetrating the membrane with an injection needle. The injected substance will impregnate the artificial bone material through the mentioned capillary ducts 2B and through the channels or passages 1E, see FIG. 11.

The first component of the artificial bone material according to the invention constitutes a rigid shape retaining frame or matrix in which the second component is integrated, for example, by initially properly mixing the components and sintering. After sintering the first component is of such a texture that it can be shaped into any desired configuration primarily into that of a natural bone or portion of a natural bone and the accessible voids can be drilled into the preshaped body.

Integration of the implanted artificial bone or bone section according to the invention takes place along the exposed surfaces inside and outside of the second component in the first component, whereby the second component induces the growth of the natural bone into the second component. For this purpose, an induction enhancing substance may be mixed into the granular material of the second component. Since the second component is rigidly connected to the first component, the latter is also connected to the existing bone tissue. The second component may disintegrate either entirely or partially as the biointegration progresses, whereby the implant becomes connected to the existing bone structure. The capillarity of the second component and its exposure on the surface of the first component ensure that the biointegration penetrates deeply into the implant.

The ratios of the volume of the first component to the volume of the second component are so selected that the second component does not weaken the first component to a compression strength less than 1000 N/cm$^2$. However, wide ranges are available, depending on the materials selected. Thus, the first component may take up as little as 5% of the total volume of the implant, while the second component takes up the remainder. However, the second component should not be less than 10% of the total volume of the implant. Thus, the first component will not take up more than 90% of the total volume and the second component will not take up more than 95% of the total volume.

According to the invention a system of storing the present artificial bone material includes the bone material and the vacuum vessel 19 in which the surgeon receives the material in an evacuated and sterilized state. The surgeon can then inject through the membrane 23 any substances as mentioned above, to impregnate the bone material in the vessel prior to implantation and then remove the impregnated material from the vessel for shaping, for example, by a surgical saw for implantation. However, it is also possible to shape the body prior to its insertion into the vacuum vessel 19.

Although the invention has been described with reference to specific example embodiments, it will be appreciated that it is intended to cover all modifications and equivalents within the scope of the appended claims.

What I claim is:

1. A synthetic bone material comprising a first component for sustaining mechanical strength and a second component for enhancing biointegration, said first component containing at least one first biomaterial having a compression strength of at least 1000 N/cm$^2$ and a first biodegradability sufficiently small to sustain said compression strength, said second component containing at least one second biomaterial having a specific surface of at least 1.5 m$^2$/gram and having a second biodegradability larger than said first biodegradability and sufficient to sustain said biointegration, said first component further having a body and a plurality of accessible voids in said body, said body and said voids together forming a tubular structure comprising a plurality of tubular channels each interconnecting a plurality of said accessible voids and said at least one second biomaterial at least partially filling said voids in said tubular structure.

2. The material of claim 1, wherein said at least one second biomaterial is natural bone tissue.

3. The material of claim 2, wherein said natural bone tissue is autologous bone tissue.

4. The material of claim 1, wherein said body is a cellular body, said cellular body and said voids together forming a honeycomb structure.

5. The material of claim 4, wherein said at least one channel is a passage in said honeycomb structure.

6. The material of claim 1, wherein said synthetic bone material is shaped as a formed body.

7. The material of claim 1, wherein said synthetic bone material has a texture which permits shaping into an anatomical configuration without destruction of said texture.

8. The material of claim 1, further comprising at least one substance selected from the group consisting of pharmaceuticals and radioisotopes and being at least substantially uniformly distributed in said synthetic bone material prior to implantation for release following implantation.

9. The material of claim 1, wherein one of said voids is adapted to receive particles of natural bone.

10. The material of claim 9, wherein said particles of natural bone are autologous bone particles.

11. The material of claim 1, wherein said synthetic bone material constitutes at least two formed bodies, said at least two formed bodies having complementary configurations permitting coupling of said at least two formed bodies to each other.

12. The material of claim 11 wherein, upon completed coupling to each other, said at least two formed bodies have the configuration of a natural bone.

13. The material of claim 1, wherein said at least one first biomaterial is a wedge-shaped body with a wedge angle alpha within a range of between about 2° and about 19°.

14. The material of claim 13, wherein said angle alpha is between about 2° and about 5°.

15. The material of claim 13, wherein said wedge-shaped body has a truncated end and a trapezoidal cross-section with a first end and a smaller second end at said truncated end.

16. The material of claim 1, wherein at least one of said first and second biomaterials is selected from the group consisting of bioceramic materials, carbon ceramics, aluminum oxide ceramics, glass ceramics, tricalciumphosphate ceramics (TCA), tetracalcium phosphate ceramics, hydroxylapatite ceramics (HA), polymethylmethacrylate, titanium, implantation alloys and biocompatible fiber composite materials, said at least one first biomaterial having voids therein in the range of 1 to 5 mm and said at least one second biomaterial having micropores within the range of 10 to 300 $\mu$m.

17. The material of claim 16, wherein said at least one first biomaterial is sintered tricalciuinphosphate (TCA) having said voids and said at least one second biomaterial is sintered hydroxylapatite (HA) at least partially occupying said voids.

18. The material of claim 16, wherein said at least one first biomaterial is sintered hydroxylapatite (HA) having said voids and said at least one second biomaterial is sintered tricalciumphosphate (TCA) at least partially occupying said voids.

19. The material of claim 1, wherein said at least one second biomaterial is a granular bioceramic material having a granule size in the range of between about 0.1 mm and 3 mm and defining interconnected pores having said specific surface of at least 1.5 $m^2$/gram.

20. The material of claim 1, wherein said synthetic bone material has a first volume and said first component has a second volume taking up between about 5% and about 90% of said first volume, said second component having a third volume taking up between about 95% and about 10% of said first volume.

21. The material of claim 1, wherein said at least one first biomaterial is a macroporous bioceramic, said at least one second biomaterial constituting a microporous bioceramic having a sufficient number of open micropores to establish said specific surface.

22. The material of claim 21, wherein said second biodegradability is at least about 20 times said first biodegradability.

23. The material of claim 21, wherein said voids of said macroporous bioceramic have dimensions within the range of between about 1 mm and 5 mm and said micropores of said microporous bioceramic have dimensions within the range of between about 10 $\mu$m and about 300 $\mu$m, said microporous bioceramic further having capillary ducts interconnecting said micropores and having diameters of up to 20 $\mu$m.

24. The material of claim 21, wherein said accessible voids in said macroporous bioceramic have a total volume smaller than a porosity which would reduce the compression strength of said macroporous bioceramic below said compression strength of at least 1000 N/$cm^2$.

* * * * *